(12) United States Patent
Addison et al.

(10) Patent No.: US 10,383,579 B2
(45) Date of Patent: Aug. 20, 2019

(54) SYSTEM AND METHOD FOR MONITORING AUTOREGULATION

(71) Applicant: COVIDIEN LP, Mansfield, MA (US)

(72) Inventors: Paul S. Addison, Edinburgh (GB);
James N. Watson, Edinburgh (GB)

(73) Assignee: Covidien LP, Mansfield, MA (US)

( * ) Notice: Subject to any disclaimer, the term of this patent is extended or adjusted under 35 U.S.C. 154(b) by 880 days.

(21) Appl. No.: 14/881,455

(22) Filed: Oct. 13, 2015

(65) Prior Publication Data
US 2016/0106372 A1 Apr. 21, 2016

Related U.S. Application Data

(60) Provisional application No. 62/064,756, filed on Oct. 16, 2014.

(51) Int. Cl.
| | |
|---|---|
| *A61B 5/1455* | (2006.01) |
| *A61B 5/0205* | (2006.01) |
| *A61B 5/00* | (2006.01) |
| *A61B 5/021* | (2006.01) |

(52) U.S. Cl.
CPC ............ *A61B 5/7221* (2013.01); *A61B 5/021* (2013.01); *A61B 5/0205* (2013.01); *A61B 5/14553* (2013.01); *A61B 5/7246* (2013.01)

(58) Field of Classification Search
CPC ... A61B 5/0205; A61B 5/1455; A61B 5/7221; A61B 5/14553; A61B 5/7246
See application file for complete search history.

(56) References Cited

U.S. PATENT DOCUMENTS

| | | | |
|---|---|---|---|
| 4,776,339 A | 10/1988 | Schreiber | |
| 5,351,685 A | 10/1994 | Potratz | |
| 5,482,034 A | 1/1996 | Lewis et al. | |
| 5,533,507 A | 7/1996 | Potratz | |
| 5,577,500 A | 11/1996 | Potratz | |
| 5,584,296 A | 12/1996 | Cui et al. | |
| 5,626,140 A | 5/1997 | Feldman et al. | |
| 5,803,910 A | 9/1998 | Potratz | |
| 5,934,277 A | 8/1999 | Mortz | |
| 6,385,471 B1 | 5/2002 | Mortz | |
| 6,438,399 B1 | 8/2002 | Kurth | |

(Continued)

FOREIGN PATENT DOCUMENTS

| | | |
|---|---|---|
| EP | 615723 A1 | 9/1994 |
| WO | WO9843071 A1 | 10/1998 |

(Continued)

OTHER PUBLICATIONS

Examination Report from counterpart European Application No. 15787810.9, dated Apr. 13, 2018, 4 pp.

(Continued)

*Primary Examiner* — Eric F Winakur
(74) *Attorney, Agent, or Firm* — Shumaker & Sieffert, P.A.

(57) ABSTRACT

A method for monitoring autoregulation includes, using a processor, receiving a blood pressure signal and an oxygen saturation signal from a patient. The method also includes determining a linear correlation between the blood pressure signal and the oxygen saturation signal and determining a significance value associated with the linear correlation. The method further includes providing a signal indicative of the patient's autoregulation status to an output device based on the linear correlation and the significance value.

20 Claims, 4 Drawing Sheets

(56) References Cited

U.S. PATENT DOCUMENTS

| | | |
|---|---|---|
| 6,453,183 B1 | 9/2002 | Walker |
| 6,505,060 B1 | 1/2003 | Norris |
| 6,510,329 B2 | 1/2003 | Heckel |
| 6,599,251 B2 | 7/2003 | Chen et al. |
| 6,668,182 B2 | 12/2003 | Hubelbank |
| 6,714,803 B1 | 3/2004 | Mortz |
| 6,725,074 B1 | 4/2004 | Kastle |
| 6,754,516 B2 | 6/2004 | Mannheimer |
| 6,896,661 B2 | 5/2005 | Dekker |
| 6,987,994 B1 | 1/2006 | Mortz |
| 7,001,337 B2 | 2/2006 | Dekker |
| 7,221,969 B2 | 5/2007 | Stoddart et al. |
| 7,268,873 B2 | 9/2007 | Sevick-Muraca et al. |
| 7,744,541 B2 | 6/2010 | Baruch et al. |
| 8,556,811 B2 | 10/2013 | Brady |
| 2004/0097797 A1 | 5/2004 | Porges et al. |
| 2004/0138540 A1 | 7/2004 | Baker, Jr. et al. |
| 2005/0004479 A1 | 1/2005 | Townsend et al. |
| 2005/0033129 A1 | 2/2005 | Edgar, Jr. et al. |
| 2005/0192488 A1 | 9/2005 | Bryenton et al. |
| 2005/0192493 A1 | 9/2005 | Wuori |
| 2007/0004977 A1 | 1/2007 | Norris |
| 2007/0049812 A1 | 3/2007 | Aoyagi et al. |
| 2007/0118036 A1 | 5/2007 | Hersh et al. |
| 2008/0081974 A1 | 4/2008 | Pav |
| 2008/0146901 A1 | 6/2008 | Katura et al. |
| 2008/0200785 A1 | 8/2008 | Fortin |
| 2008/0228053 A1 | 9/2008 | Wang et al. |
| 2009/0326386 A1 | 12/2009 | Sethi et al. |
| 2010/0010322 A1 | 1/2010 | Brady |
| 2010/0030054 A1 | 2/2010 | Baruch et al. |
| 2010/0049082 A1 | 2/2010 | Hu et al. |
| 2010/0130873 A1 | 5/2010 | Yuen et al. |
| 2011/0046459 A1 | 2/2011 | Zhang et al. |
| 2011/0105912 A1 | 5/2011 | Widman et al. |
| 2012/0149994 A1 | 6/2012 | Luczyk et al. |
| 2012/0253211 A1 | 10/2012 | Brady et al. |
| 2012/0271130 A1 | 10/2012 | Benni |
| 2013/0190632 A1 | 7/2013 | Baruch et al. |
| 2014/0073888 A1 | 3/2014 | Sethi et al. |
| 2014/0275818 A1 | 9/2014 | Kassem et al. |
| 2014/0278285 A1 | 9/2014 | Marmarelis et al. |
| 2016/0324425 A1 | 11/2016 | Addison et al. |
| 2016/0345913 A1 | 12/2016 | Montgomery et al. |
| 2016/0367197 A1 | 12/2016 | Addison et al. |
| 2017/0000395 A1 | 1/2017 | Addison et al. |
| 2017/0000423 A1 | 1/2017 | Addison et al. |
| 2017/0095161 A1 | 4/2017 | Addison et al. |
| 2017/0105631 A1 | 4/2017 | Addison et al. |
| 2017/0105672 A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | 2008097411 A1 | 8/2008 |
| WO | WO2008097411 A1 | 8/2008 |
| WO | WO2016182853 A1 | 11/2016 |

OTHER PUBLICATIONS

International Preliminary Report on Patentability from International Application No. PCT/US2015/055548, dated Apr. 18, 2017, 7 pp.
Erik D. Gommer et al.; "Dynamic cerebral autoregulation: different signal processing methods without influence on results and reproducibility"; Medical & Biological Engineering & Computer; vol. 48, No. 12, Nov. 4, 2010; pp. 1243-1250.
International Search Report & Written Opinion for PCT Application No. PCT/US2015/055548 dated Jan. 7, 2016; 12 pages.
U.S. Appl. No. 15/666,167, filed Aug. 1, 2017, naming inventors Addison et al.
Communication Pursuant to Rules 161(1) and 162 EPC dated May 23, 2017 from counterpart European Application No. 15787810.9, 5 pp.
International Search Report and Written Opinion of International Application No. PCT/US2015/055548, dated Jan. 7, 2016, 10 pp.
Addison, P. S., et al.; "Low-Oscillation Complex Wavelets," Journal of Sound and Vibration, 2002, vol. 254, Elsevier Science Ltd., pp. 1-30.
Addison, P. S.; "The Illustrated Wavelet Transform Handbook," 2002, IOP Publishing Ltd., Bristol, UK, Ch. 2.
Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).
Barreto, Armando B., et al.; "Adaptive LMS Delay Measurement in dual Blood Volume Pulse Signals for Non-Invasive Monitoring," IEEE, pp. 117-120 (1997).
Bassan, Haim, et al.; "Identification of pressure passive cerebral perfusion and its mediators after infant cardiac surgery," Pediatric Research Foundation, vol. 57, No. 1, 2005; pp. 35-41.
Belal, Suliman Yousef, et al.; "A fuzzy system for detecting distorted plethysmogram pulses in neonates and paediatric patients," Physiol. Meas., vol. 22, pp. 397-412 (2001).
Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.
Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.
Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).
Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.
Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.
Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.
Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).
Chan, K.W., et al.; "17.3: Adaptive Reduction of Motion Artifact from Photoplethysmographic Recordings using a Variable Step-Size LMS Filter," IEEE, pp. 1343-1346 (2002)+A10.
Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.
Chen, Liangyou, et al.; "IS respiration-induced variation in the photoplethysmogram associated with major hypovolemia in patients with actue tramatic injuries," SHOCK, vol. 34, No. 5, pp. 455-460 (2010).
Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.
Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.
Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

(56) References Cited

OTHER PUBLICATIONS

Cysewska-Sobusaik, Anna; "Metrological Problems With noninvasive Transillumination of Living Tissues," *Proceedings of SPIE*, vol. 4515, pp. 15-24 (2001).
Czosnyka, Marek, et al.; "Monitoring of cerebrovascular autoregulation: Facts, Myths, and Missing Links," Neurocrit Care (2009) 10:373-386.
Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.
Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.
Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.
East, Christine E., et al.; "Fetal Oxygen Saturation and Uterine Contractions During Labor," *American Journal of Perinatology*, vol. 15, No. 6, pp. 345-349 (Jun. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.
Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.
Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
Ge, Z.; "Significance tests for the wavelet cross spectrum and wavelet linear coherence," Annales Geophysicae, 2008, 26, Copernicus Publications on behalf of European Geosciences Union, pp. 3819-3829.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Goldman, Julian M.; "Masimo Signal Extraction Pulse Oximetry," *Journal of Clinical Monitoring and Computing*, vol. 16, pp. 475-483 (2000).
Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.
Hamilton, Patrick S., et al.; "Effect of Adaptive Motion-Artifact Reduction on QRS Detection," *Biomedical Instrumentation & Technology*, pp. 197-202 (May-Jun. 2000).
Huang, J., et al.; "Low Power Motion Tolerant Pulse Oximetry," Anesthesia & Analgesia 2002 94: S103.
Johansson, A.; "Neural network for photoplethysmographic respiratory rate monitoring," *Medical & Biological Engineering & Computing*, vol. 41, pp. 242-248 (2003).
Kaestle, S.; "Determining Artefact Sensitivity of New Pulse Oximeters in Laboratory Using Signals Obtained from Patient," *Biomedizinische Technik*, vol. 45 (2000).
Kim, J.M., et al.; "Signal Processing Using Fourier & Wavelet Transform for pulse oximetry," pp. II-310-II-311 (2001).
Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Leahy, Martin J., et al.; "Sensor Validation in Biomedical Applications," *IFAC Modelling and Control in Biomedical Systems*, Warwick, UK; pp. 221-226 (1997).
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Lee, Jennifer K., et al.; A pilot study of cerebrovascular reactivity autoregulation after pediatric cardiac arrest, Resuscitation 85, 2014, Elsevier Ireland Ltd., pp. 1387-1393.
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Montgomery, Dean, et al.; "Data cluestering methods for the determination of cerebral autoregulation functionality," Journal of Clinical Monitoring and Computing, vol. 30, No. 5, Sep. 16, 2015, pp. 661-668.
Morren, G., et al.; "Detection of autoregulation in the brain of premature infants using a novel subspace-based technique," 23rd Annual International Conference of IEEE Engineering in Medicine and Biology Society, Oct. 2001; pp. 1-4.
Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.
Neumann, R., et al.; "Fourier Artifact suppression Technology Provides Reliable $SpO_2$," Anesthesia & Analgesia 2002, 94: S105.
Obrig, Hellmuth, et al.; "Spontaneous low frequency oscillations of cerebral heodynamics and metabolism in human adults," NeuroImage 12, 623-639 (2000).
Odagiri, Y.; "Pulse Wave Measuring Device," *Micromechatronics*, vol. 42, No. 3, pp. 6-11 (published Sep. 1998) (Article in Japanese—contains English summary of article).
Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).
Payne, Stephen J., et al.; "Tissue Oxygenation Index as a Measure of Cerebral Autoregulation," Biomedial Engineering, Feb. 2004, Innsbruck, Austria, pp. 546-550.
Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
Reinhard, Matthias, et al.; "Oscillatory cerebral hemodynamics—the macro- vs. microvascular level," Journal of the Neurological Sciences 250 (2006) 103-109.
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.
Shamir, M., et al.; "Pulse oximetry plethysmographic waveform during changes in blood volume," British Journal of Anaesthesia 82(2): 178-81 (1999).

(56) References Cited

OTHER PUBLICATIONS

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," NEURO-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu, Dongmei, et al.; "Na*/H* Exchange inhibition delays the onset of hypovolemic circulatory shock in pigs," Shock, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

Chuan et al., "Is cerebrovascular autoregulation associated with outcomes after major noncardiac surgery? A prospective observational pilot study," Acta Anaesthesiol Scand., Aug. 5, 2018, 10 pp.

Response to Examination Report dated Apr. 12, 2018, from counterpart European Application No. 15787810.9, filed Aug. 8, 2018, 14 pp.

Summons to Attend Oral Proceedings pursuant to Rule 115(1) EPC from counterpart European Patent Application No. 15787810.9, dated Mar. 12, 2018, 7 pp.

SYSTEM AND METHOD FOR MONITORING AUTOREGULATION

CROSS REFERENCE TO RELATED APPLICATION

This application claims priority from and the benefit of U.S. Provisional Patent Application No. 62/064,756, filed Oct. 16, 2014, entitled "System and Method for Monitoring Autoregulation," which is incorporated by reference herein in its entirety.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperminia, which may result in swelling of the brain or edema.

Some existing systems for monitoring autoregulation may determine a patient's autoregulation status based on various physiological signals. Such physiological signals may be subject to various sources of error, such as noise. However, existing systems for monitoring autoregulation may not consider a quality of the physiological signals used to determine the patient's autoregulation status. Furthermore, existing systems may not evaluate a correlation between the various physiological signals to determine whether the calculated autoregulation status is reliable. Accordingly, the autoregulation status determined by such existing systems may be inaccurate or unreliable.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In accordance with the present disclosure, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) may be derived based at least in part on a linear correlation between the patient's blood pressure and oxygen saturation. Further, the disclosed systems and methods may determine a significance value (p value) related to the linear correlation between the blood pressure and the oxygen saturation. The p value may enable the system to determine whether the COx is reliable or unreliable. For example, the p value may enable the system to identify certain portions of the COx that are adversely affected by noise, and therefore, unreliable. In some embodiments, the system may be configured to ignore or discard the portions of the COx that are unreliable or take other remedial actions to provide accurate autoregulation information to the medical professional, as discussed in more detail below.

Figure 1:
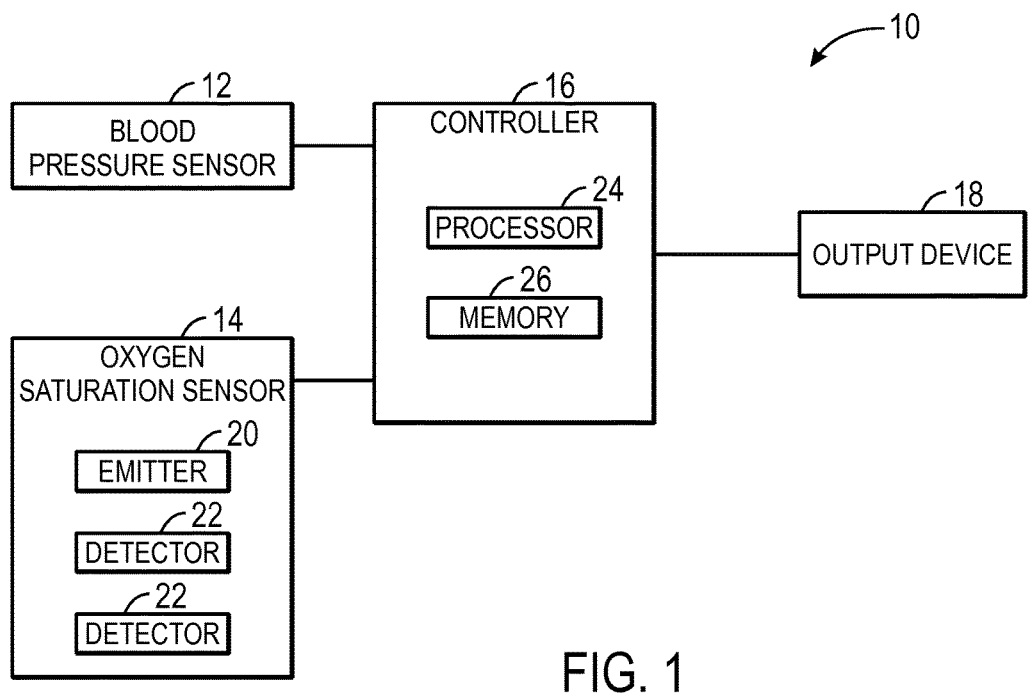
FIG. 1 is a block diagram of an embodiment of a system for monitoring a patient's autoregulation.

FIG. 1 illustrates an embodiment of a system 10 for monitoring autoregulation. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex).

In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In some embodiments, light drive circuitry (e.g., within a monitor) may provide a light drive signal to drive the emitter 20 and to cause the emitter 20 to emit light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 20. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

As discussed in more detail below, the controller 16 may be configured to determine a cerebral oximetry index (COx) based on the blood pressure signal and the oxygen saturation signal. The COx is indicative of vascular reactivity, which is related to cerebral blood vessels' ability to control proper blood flow, via vasoconstriction (a narrowing of the blood vessel) and/or vasodilation (expansion of the blood vessel), for example. Thus, the COx is also indicative of whether the patient's autoregulation is impaired. The controller 16 may derive the COx by determining a linear correlation between blood pressure measurements and oxygen saturation measurements. The linear correlation may be based on a Pearson coefficient, for example. The Pearson coefficient may be defined as the covariance of the measured blood pressure (e.g., arterial blood pressure) and oxygen saturation divided by the product of their standard deviations. The result of the linear correlation may be a regression line between oxygen saturation measurements and blood pressure measurements, and the slope of the regression line may be indicative of the patient's autoregulation status. In one possible implementation, a regression line with a relatively flat or negative slope (e.g., regional oxygen saturation increases after blood pressure decreases) may suggest that cerebral autoregulation is working properly, while a regression line with a positive slope (e.g., regional oxygen saturation remains the same or decreases after blood pressure decreases) may suggest that the cerebral autoregulation is impaired.

The controller 16 may determine a value of the COx, which may be between −1 and 1, inclusive, where −1 represents total negative correlation, +1 represents total positive correlation, and 0 represents the absence of correlation between the blood pressure measurements and the oxygen saturation measurements. Thus, COx values between −1 and 0 may suggest that cerebral autoregulation is working properly, while COx values between 0 and 1 may suggest that the cerebral autoregulation is impaired. In some cases, a predetermined threshold between 0 and 1 may be utilized to determine whether the patient's autoregulation is impaired. For example, in some embodiments, the controller 16 may be configured to determine that the patient's autoregulation is impaired when the COx value is greater than 0.1, 0.2, 0.3, 0.4, 0.5, 0.6, 0.7, 0.8, or 0.9. Accordingly, the controller 16 may be configured to determine the COx value and/or the patient's autoregulation status based on the linear correlation between the blood pressure measurements and oxygen saturation measurements obtained by the blood pressure sensor 12 and the oxygen saturation sensor 14, respectively.

As discussed in more detail below, the controller 16 may be configured to determine a significance value (e.g., a p value) associated with the linear correlation of the blood pressure measurements and the oxygen saturation measurements. The p value may indicate whether certain COx values, or portions of a COx signal generated based on such values, are reliable or unreliable. For example, the p value may enable the controller 16 to identify portions of the COx signal that are adversely affected by noise, and which are therefore unreliable. As discussed in more detail below, the controller 16 may be configured to remove or discard the unreliable portions of the COx signal and/or take other appropriate remedial actions.

In some embodiments, the controller 16 may be configured to determine or to receive (e.g., from an intermediate processing device, such as the blood pressure monitor or an oxygen saturation monitor, or the like, or from sensors having such processing capabilities) one or more quality metrics associated with the blood pressure signal and/or the oxygen saturation signal. The quality metric may be indicative of the accuracy of the signal and may be calculated based on one or more signal quality indicators. Any suitable signal quality indicators may be considered, including a signal measure indicative of a low light level; a signal measure indicative of an arterial pulse shape; a signal measure indicative of the high frequency signal component in the measured value; a signal measure indicative of a consistency of a pulse shape; a signal measure indicative of an arterial pulse amplitude; and a signal measure indicative of a period of an arterial pulse, for example. These various indicators provide an indirect assessment of the presence of known error sources in blood pressure or oxygen saturation signals, which include optical interference between the sensor and the tissue location, physical movement of the patient, and/or improper tissue-to-sensor positioning, for example.

The value of the quality metric may then be compared to a quality metric threshold. In some embodiments, the controller 16 may only proceed to determine and/or output the COx while the quality metric is above the threshold, thus indicating that the quality of one or both signals is adequate. In some embodiments, the controller 16 may not calculate and/or output the COx while the quality metric is below the threshold, thus indicating that the quality of one or both such signals is inadequate. It should be understood that in certain embodiments, multiple quality metrics may be compared to multiple corresponding quality metric thresholds. In some such embodiments, the controller 16 may only proceed to determine and/or output the COx while one or more of the multiple quality metrics are above the corresponding quality metric thresholds, thus indicating that the quality of one or bath signals is adequate. In some embodiments, the controller 16 may not calculate and/or output the COx while one or more of the multiple quality metrics is below the corresponding quality metric thresholds, thus indicating that the quality of one or both such signals is inadequate. In some cases, the controller 16 may only determine the COx while the one or more quality metrics indicate that the quality of one or both signals is adequate, and then may only output the COx or indication of the patient's autoregulation status while the p value indicates that the COx is reliable.

In the illustrated embodiment, the controller 16 includes a processor 24 and a memory device 26. The controller 16 may also include one or more storage devices. The processor 24 may be used to execute software, such as software for carrying out any of the techniques disclosed herein, such as processing the blood pressure signals and/or oxygen saturation signals, determining signal quality metrics, comparing signal quality metrics to one or more thresholds, determining the COx value, calculating a significance value (p value), comparing the p value to the predetermined threshold (e.g., p value threshold), carrying out appropriate remedial actions, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for carrying out any of the techniques discloses herein, such as processing the blood pressure signal and/or the oxygen saturation signal, determining signal quality metrics, comparing signal quality metrics to one or more thresholds, determining the COx and/or the p value, comparing the p value to the predetermined threshold, and/or taking appropriate remedial actions. The storage device(s) (e.g., non-volatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the COx, the p value, etc.), instructions (e.g., software or firmware for processing the blood pressure signal and/or the oxygen saturation signal, determining the COx and/or the p value, and/or taking appropriate remedial actions), predetermined thresholds, and any other suitable data.

As shown, the system 10 includes the output device 18. In some embodiments, the controller 16 may be configured to provide signals indicative of the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the patient's autoregulation status, the alarm signal, or the like) from the controller 16 and visually and/or audibly output information indicative of the patient's autoregulation status (e.g., the COx value, the COx signal, an alarm, or the like). For instance, the output device 18 may include a display configured to provide a visual representation of the patient's autoregulation status and/or the alarm signal as determined by the controller 16. Additionally or alternatively, the output device 18 may include an audio device configured to provide sounds in accordance with the alarm signal, the patient's autoregulation status, or both. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

Figure 2:
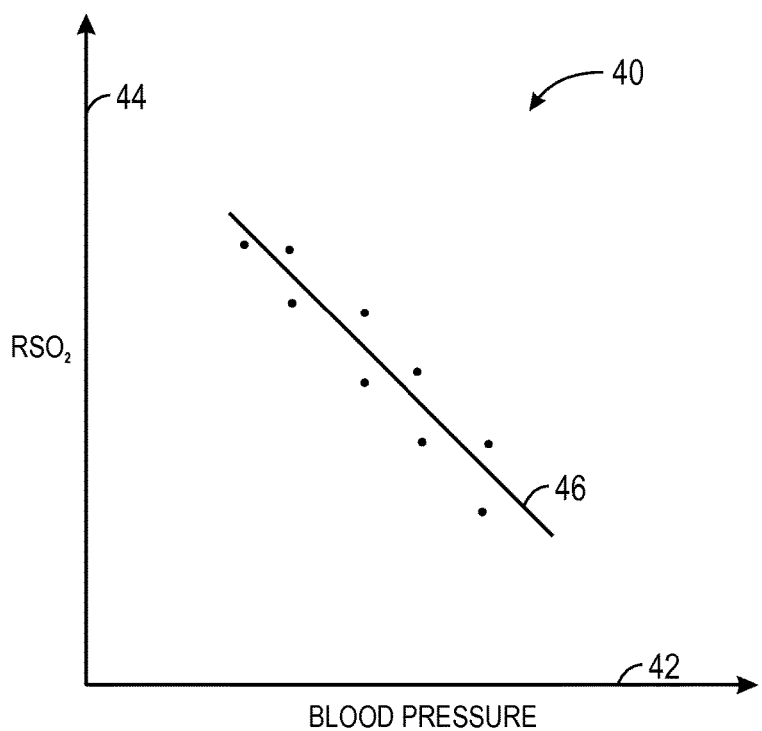
FIG. 2 is an example of a graph illustrating a linear correlation between oxygen saturation values and blood pressure values.

FIG. 2 is an example of a graph 40 illustrating a linear correlation between blood pressure measurements 42 (e.g., arterial blood pressure measurements) and oxygen saturation measurements 44. The result of the linear correlation may be a regression line 46 between the blood pressure measurements 42 and the oxygen saturation measurements 44, and the slope of the regression line 46 may be indicative of the patient's autoregulation status. In the illustrated example, the slope of the regression line 46 is negative and, thus, the COx value is between −1 and 0, which as discussed above, may indicate proper autoregulation. In such cases, the controller 16 may determine that the patient's cerebral autoregulation is functioning properly and may generate and/or output an appropriate signal indicative of the patient's autoregulation status to the output device 18, for example. However, when the regression line 46 has a positive slope and the COx value is between 0 and 1 or above some predetermined threshold (e.g., 0.1, 0.2, 0.3, 0.4, 0.5, 0.6, 0.7, 0.8, or 0.9, as discussed above), the controller 16 may determine that the patient's autoregulation is impaired and may generate and/or output the appropriate signal indicative of the patient's autoregulation status. As discussed in more detail below, the controller 16 may also determine the p value associated with the linear correlation. In such cases, the controller 16 may utilize the p value to determine whether the COx value is reliable or unreliable, and may remove or discard unreliable COx values and/or take other appropriate remedial action when the COx value is unreliable. In some instances, the signal indicative of the patient's autoregulation status may be displayed as a graph similar to the graph 40 of FIG. 2 shown on the output device 18 for presentation to a treating physician.

Figure 3:
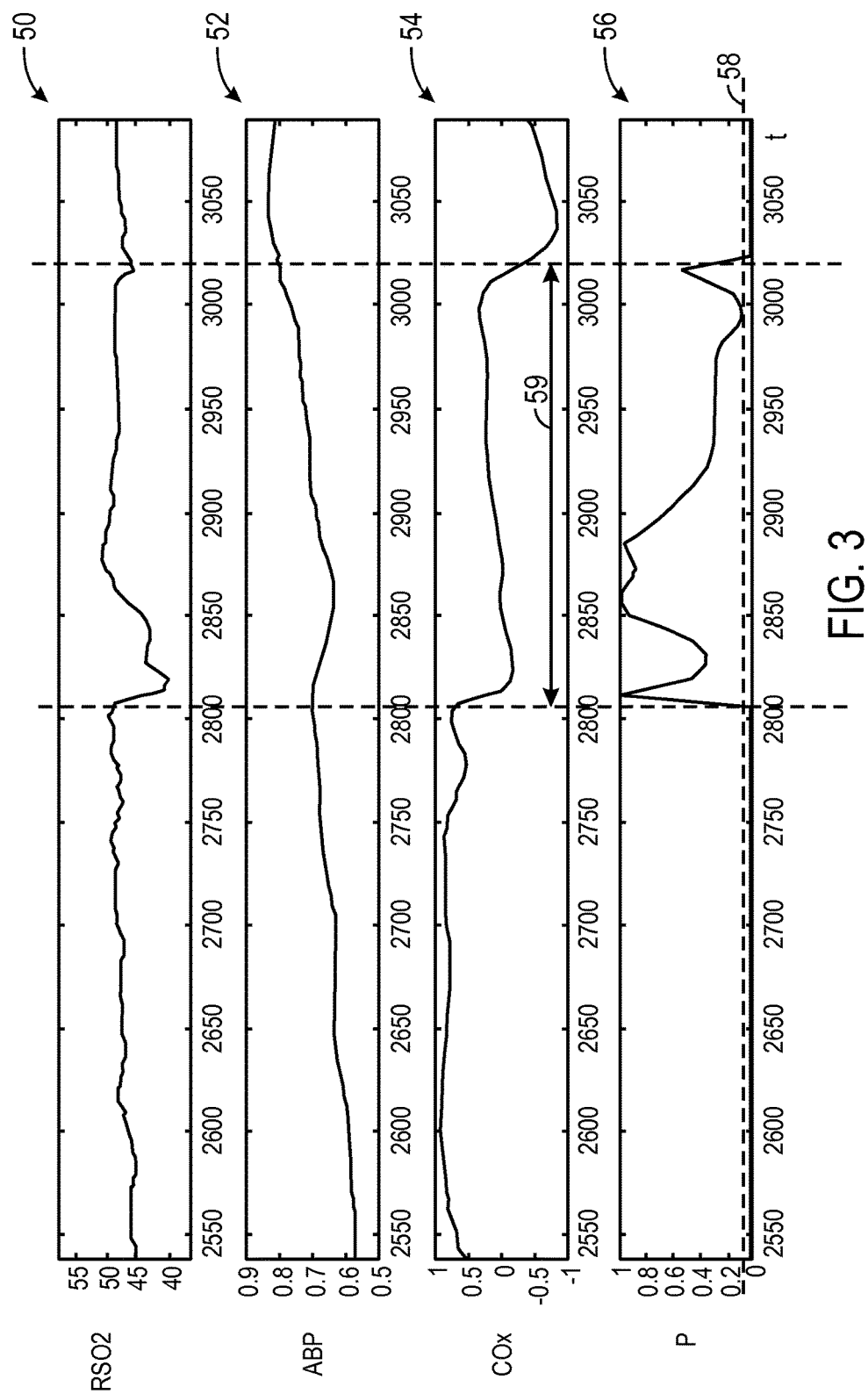
FIG. 3. is an example of a series of graphs illustrating oxygen saturation, blood pressure, cerebral oximetry index, and p value over time.

FIG. 3 is an example of a series of graphs illustrating an oxygen saturation signal 50, a blood pressure signal 52, a COx signal 54, and p values 56. The oxygen saturation signal 50 may be obtained by the oxygen saturation sensor 14 over a period of time, while the blood pressure signal 52 may be obtained by the blood pressure sensor 12 over the period of time. The oxygen saturation signal 50 and the blood pressure signal 52 may be provided to the controller 16. The controller 16 is configured to determine the COx signal 54 based on the linear correlation between the oxygen saturation signal 50 and the blood pressure signal 52, as discussed above. In certain embodiments, the controller 16 is also configured to determine the p value associated with the linear correlation.

During patient monitoring, the oxygen saturation signal 50 and/or the blood pressure signal 52 are often affected by noise. In some cases, certain segments of the oxygen saturation signal 50 and/or the blood pressure signal 52 are affected by noise to the extent that portions of the determined COx signal 54 may not be reliable or accurate. In the disclosed embodiments, the controller 16 may identify portions of the COx signal 54 that are unreliable based on the p values 56. For example, the controller 16 may be configured to compare the p value 56 to a predetermined threshold 58 (e.g., 0.01, 0.05, or the like) and may be configured to determine that a portion of the COx signal 54 is unreliable when the corresponding p value is above the predetermined threshold. With respect to the data in FIG. 3, for example, the controller 16 may determine that the portion 59 of the COx signal 54 is unreliable as the corresponding p value 56 is above the predetermined threshold 58.

In certain cases, the controller 16 may be configured to remove or discard the unreliable COx signal 54 and/or take some other remedial action when the p value 56 is above the predetermined threshold 58. For example, the controller 16 may not output the COx signal 54 or the signal indicative of the patient's autoregulation status while the p value 56 is above the predetermined threshold 58. In some cases, the controller 16 may cause the output device 18 to display a blank display screen or provide an appropriate visual or audible indication that the COx signal 54 is unavailable. In certain embodiments, the controller 16 may hold or maintain the COx value immediately preceding the segment determined to be unreliable, and thus may cause the output device 18 to show the most recent reliable COx signal 54 for a set period of time or until the p value 56 returns to an acceptable level. In some embodiments, the controller 16 may be configured to average the unreliable COx value(s) with the most recent reliable COx value(s), and may cause the output device 18 to provide an appropriate visual or audible indication of this average COx value. In some embodiments, when the controller 16 determines that the p value 56 is below the predetermined threshold 58, the controller 16 may cause the output device 18 to provide a visual or audible indication that the COx signal 54 is reliable.

Figure 4:
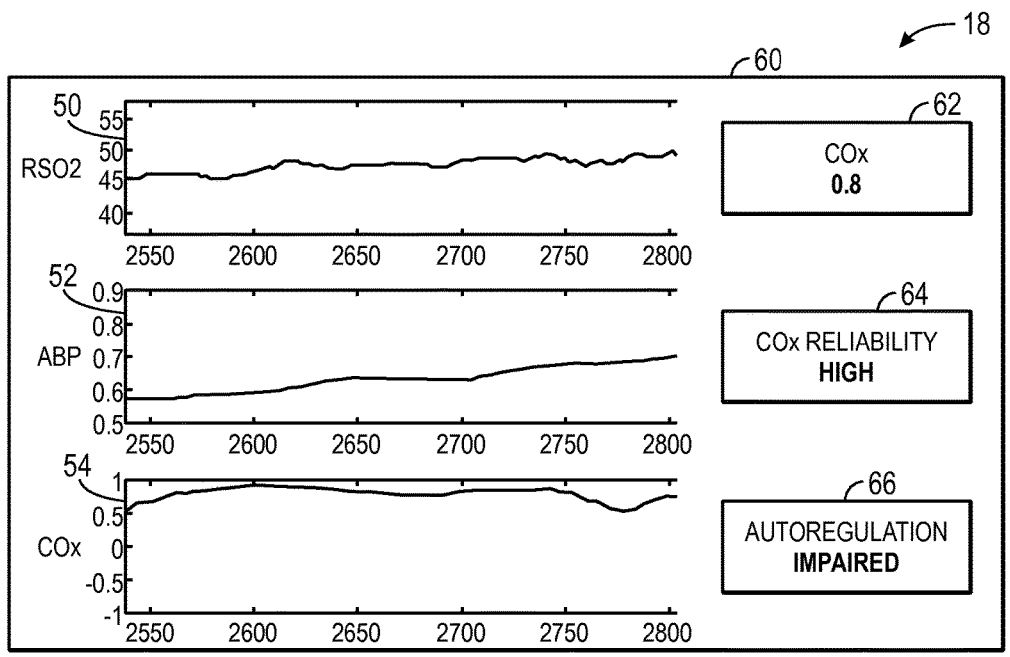
FIG. 4 is an embodiment of a display configured to display various information related to an autoregulation status of a patient.

FIG. 4 is an embodiment of a display 60 of the output device 18 that is configured to display various information related to the COx. As shown, the display 60 may be configured to provide a representation of the oxygen saturation signal 50, a representation of the blood pressure signal 52, and a representation of the COx signal 54. In some embodiments, the display 60 may provide a representation of the p value, in a similar manner shown in FIG. 3. As shown, the display 60 may also be configured to provide a COx value 62, which may be updated continuously or at predetermined intervals. In some embodiments, the display 60 may provide a COx reliability indication 64 related to whether the COx value 62 and COx signal 54 are reliable, which may be determined based on the p value, as discussed above. For example, in the illustrated embodiment, the display 60 indicates that the COx reliability 64 is high (e.g., 75, 95, 99 percent confident, or the like). However, while the p value is above the predetermined p value threshold, the display 60 may not provide the COx value 62 and/or may provide an indication that the COx value 62 is unavailable. In such cases, the display 60 may provide an indication that the COx reliability 64 is low or unacceptable (e.g., below 25, 50, 75, 95, 99 percent confidence, or the like). In some cases, while the p value is above the predetermined p value threshold, the display 60 may continue to provide the current or last reliable COx value 62 (e.g., 0.8) for a predetermined time or until the p value falls below the predetermined threshold. In such cases, the display 60 may also provide an indication that the COx value 62 is a prior value and/or that the COx reliability 64 is low or acceptable. In other cases, the display 60 may provide an average COx value 62 (e.g., of the current COx value and the prior reliable COx value(s)), and in such cases, the display 60 may also provide an indication that the COx value 62 is an average COx value. Further, in such cases, the display 60 may also provide an indication that the COx reliability 64 is low or acceptable (e.g., below 25, 50, 75, 95, 99 percent confidence or the like). As noted above, the COx value 62 of 0.8 may indicate impaired autoregulation, and thus the display 60 may be configured to provide such an indication of the patient's autoregulation status 66. While the COx value 62 is below the COx value threshold (e.g., 0.5 or the like) and/or while the p value is below the predetermined threshold, the display 60 may indicate that the autoregulation is functioning properly.

Figure 5:
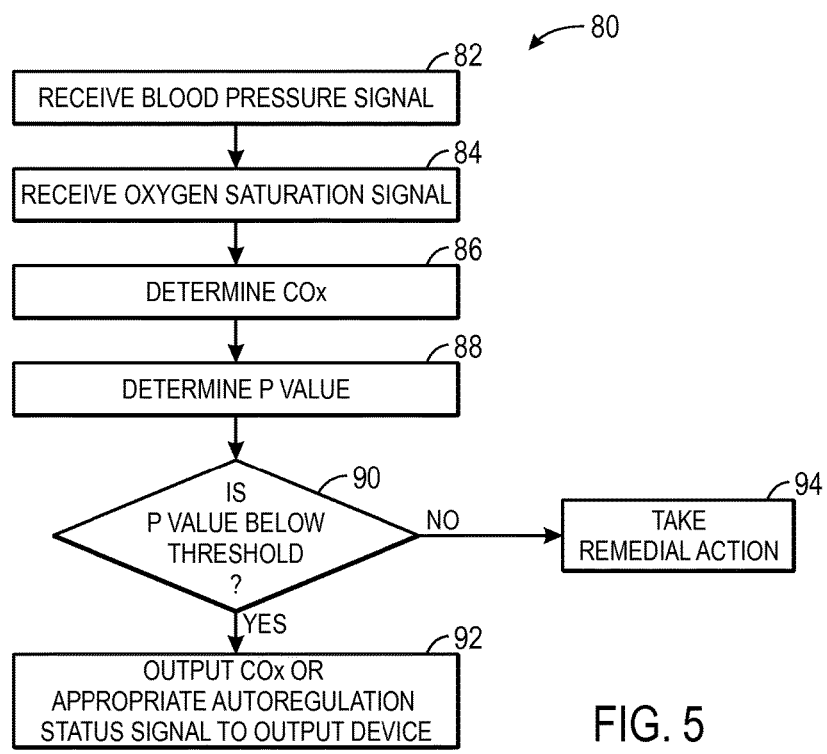
FIG. 5 is a process flow diagram of a method of monitoring autoregulation, in accordance with an embodiment.

FIG. 5 is a process flow diagram of a method 80 of monitoring autoregulation, in accordance with an embodiment. Some or all of the steps of the method 80 may be implemented by the controller 16 (e.g., the processor 24 of the controller 16) of FIG. 1, for example, to determine whether the patient's autoregulation is impaired and/or to take an appropriate remedial action. In step 82, the controller 16 may receive the blood pressure signal (e.g., arterial blood pressure signal). In some embodiments, the controller 16 may receive the blood pressure signal from the blood pressure sensor 12, as set forth above. In step 84, the controller 16 may receive the oxygen saturation signal. In some embodiments, the controller 16 may receive the oxygen saturation signal from the oxygen saturation sensor 14, as set forth above.

In step 86, the controller 16 may determine the COx based on the linear correlation between blood pressure measurements of the blood pressure signal and the oxygen saturation measurements of the oxygen saturation signal. In step 88, the controller 16 may determine the p value associated with the linear correlation. In decision step 90, the controller may determine whether the p value is above a predetermined threshold. The predetermined threshold may be any suitable threshold, such as 0.01 or 0.05, for example. As noted above, the predetermined threshold may be stored in the memory 26 or other suitable storage device of the controller 16. If the p value is below the predetermined threshold, the controller 16 may determine that the COx is reliable (e.g., a high or acceptable confidence level in the COx) and may output the COx or a signal indicative of the patient's autoregulation status to the output device 18, in step 92. In such cases, the controller 16 may cause the output device 18 to present a visual or audible indication of the COx or the patient's autoregulation status. Furthermore, in some such cases, the controller 16 may cause the output device 18 to present a visual or audible indication that the COx is reliable.

However, if the p value is above the predetermined threshold, the controller 16 may determine that the COx is unreliable (e.g., a low or unacceptable confidence level in the COx) and may take some appropriate remedial action, in step 94. For example, the controller 16 may discard the COx and/or may not provide the COx to the output device 18, while the p value is above the predetermined threshold. In some cases, the controller 16 may cause the output device 18 to display a blank display screen or provide an appropriate visual or audible indication that the COx is unavailable. In certain embodiments, the controller 16 may hold or maintain the COx value immediately preceding the segment determined to be unreliable, and thus may cause the output device 18 to show the most recent reliable COx value or COx signal 54 for a set period of time (e.g., 5, 10, 20, 30, 40, 50, 60 seconds or more) or until the p value 56 returns to an acceptable level. In some such cases, the controller 16 may also cause the output device 18 to provide a visual or audible indication that the current COx is unavailable and/or that the displayed COx value or COx signal 54 was previously obtained. In some embodiments, the controller 16 may be configured to average the unreliable COx value(s) with the most recent reliable COx value(s), and may cause the output device 18 to provide an appropriate visual or audible indication of this average COx value. In some such cases, the controller 16 may also cause the output device 18 to provide a visual or audible indication that the provided COx value is an average COx value and/or of a low or acceptable confidence level in the provided COx value.

Figure 6:
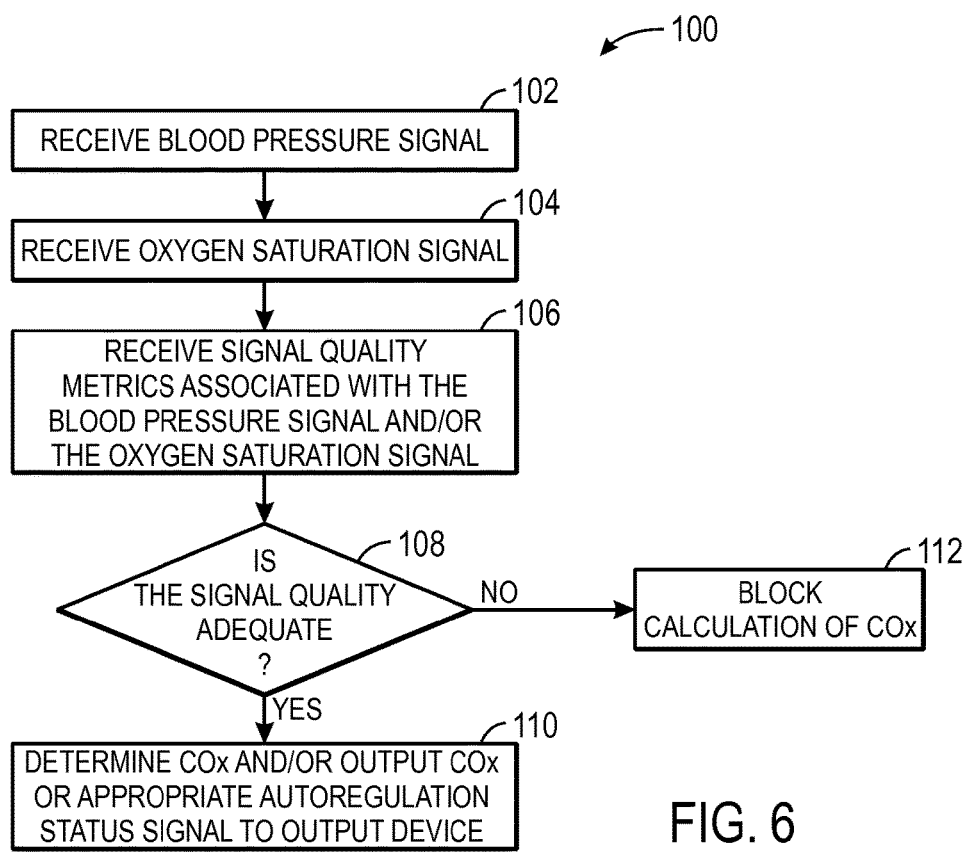
FIG. 6 is a process flow diagram of a method of monitoring autoregulation based on signal quality metrics, in accordance with an embodiment.

FIG. 6 is a process flow diagram of a method 100 of monitoring autoregulation using signal quality metrics associated with the blood pressure signal and the oxygen saturation signal, in accordance with an embodiment. Some or all of the steps of the method 100 may be implemented by the controller 16 (e.g., the processor 24 of the controller 16) of FIG. 1, for example, to determine whether the patient's autoregulation is impaired. In step 102, the controller 16 may receive the blood pressure signal (e.g., arterial blood pressure signal). In some embodiments, the controller 16 may receive the blood pressure signal from the blood pressure sensor 12, as set forth above. In step 104, the controller 16 may receive the oxygen saturation signal. In some embodiments, the controller 16 may receive the oxygen saturation signal from the oxygen saturation sensor 14, as set forth above.

As noted above, during patient monitoring, the blood pressure signal and the oxygen saturation signal may be affected by noise. Accordingly, in step 106, the controller 16 may receive signal quality metrics associated with the blood pressure signal and/or the oxygen saturation signal. Such signal quality metrics may be indicative of the accuracy of such signals and may be calculated based on one or more signal quality indicators. Any suitable signal quality indicators may be considered, including those listed above, for example. The signal quality metrics may be determined by any suitable processing device, such as a blood pressure monitor or an oxygen saturation monitor. In some embodiments, the blood pressure sensor 12 and/or the oxygen saturation sensor 14 may have processing capabilities, and thus may provide the signal quality metrics directly to the controller 16. In some cases, the controller 16 itself may be configured to determine the signal quality metrics.

In decision step 108, the controller 16 may determine whether the quality of the blood pressure signal and/or the oxygen saturation signal are adequate. While the signal quality metrics indicate that the quality of one or both signals is adequate, the controller 16 may proceed to determine the COx and/or to output the COx and/or the signal indicative of the patient's autoregulation status to the output device 18, in step 110. However, while the quality metrics indicate that the quality of one or both such signals is inadequate, the controller may not calculate and/or output the COx, in step 112. In some embodiments, the controller 16 may implement both of the techniques illustrated in FIG. 5 and FIG. 6 to provide an accurate and/or reliable indication of the patient's autoregulation status. For example, in some embodiments, the controller 16 may only determine the COx while the signal quality metrics indicate adequate signal quality as shown in the method of FIG. 6, and the controller 16 may then calculate the p value associated with the linear correlation to determine whether the COx is reliable and take appropriate actions, as shown in the method of FIG. 5. In some embodiments, the controller 16 may only output the COx while the signal quality metrics indicate adequate signal quality as shown in the method of FIG. 6, and while the p value is below the predetermined threshold, as discussed above with respect to FIG. 5.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method for monitoring autoregulation, the method comprising:
   receiving, by one or more processors, a blood pressure signal indicative of a blood pressure of a patient and an oxygen saturation signal indicative of blood oxygen saturation of the patient;
   determining, by the one or more processors, a linear correlation between the blood pressure signal and the oxygen saturation signal;
   determining, by the one or more processors, a significance value associated with the linear correlation, wherein the significance value comprises a p-value; and
   providing, by the one or more processors, a signal indicative of the patient's autoregulation status to an output device based on the linear correlation and the significance value.

2. The method of claim 1, comprising:
   determining, by the one or more processors, the significance value is below a predetermined threshold; and
   providing, by the one or more processors, a cerebral oximetry index value to the output device only while the significance value is below the predetermined threshold.

3. The method of claim 1, comprising:
   determining, by the one or more processors, the significance value is above a predetermined threshold; and
   providing, by the one or more processors, a prior reliable cerebral oximetry index value to the output device in response to determining the significance value is above the predetermined threshold.

4. The method of claim 1, comprising:
   determining, by the one or more processors, the significance value is above a predetermined threshold; and
   averaging, by the one or more processors, a current cerebral oximetry index value with a prior reliable cerebral oximetry index value to generate an average cerebral oximetry index value in response to determining the significance value is above the predetermined threshold.

5. The method of claim 4, comprising providing the average cerebral oximetry index value to the output device.

6. The method of claim 1, wherein receiving the oxygen saturation signal comprises receiving the oxygen saturation signal from a regional saturation sensor comprising at least one emitter and a plurality of detectors.

7. The method of claim 1, comprising receiving a signal quality metric related to the blood pressure signal, the oxygen saturation signal, or both.

8. The method of claim 7, comprising:
   comparing, by the one or more processors, the signal quality metric to a signal quality metric threshold; and
   determining, by the one or more processors, the linear correlation between the blood pressure signal and the oxygen saturation signal only while the signal quality metric is above the signal quality metric threshold.

9. A monitor for monitoring autoregulation, the monitor comprising:
   an output device; and
   one or more processors configured to:
   receive a blood pressure signal indicative of a blood pressure of a patient and an oxygen saturation signal indicative of blood oxygen saturation of the patient;
   determine a linear correlation between the blood pressure signal and the oxygen saturation signal;
   determine a significance value associated with the linear correlation, wherein the significance value comprises a p-value; and
   provide a signal indicative of the patient's autoregulation status to the output device based on the linear correlation and the significance value.

10. The monitor of claim 9, wherein the one or more processors are configured to:
    determine the significance value is below a predetermined threshold; and
    provide a cerebral oximetry index value to the output device only while the significance value is below the predetermined threshold.

11. The monitor of claim 9, wherein the one or more processors are configured to:
    determine the significance value is above a predetermined threshold; and
    provide a prior reliable cerebral oximetry index value to the output device in response to determining the significance value is above the predetermined threshold.

12. The monitor of claim 9, wherein the one or more processors are configured to:
    determine the significance value is above a predetermined threshold;
    average a current cerebral oximetry index value with a prior reliable cerebral oximetry index value to generate an average cerebral oximetry index value in response to determining the significance value is above the predetermined threshold; and
    provide the average cerebral oximetry index value to the output device.

13. The monitor of claim 9, wherein the one or more processors are configured to receive the oxygen saturation signal from a regional saturation sensor comprising at least one emitter and plurality of detectors.

14. The monitor of claim 9, wherein the one or more processors are configured to receive a signal quality metric related to the blood pressure signal, the oxygen saturation signal, or both.

15. The monitor of claim 14, wherein the one or more processors are configured to:
    compare the signal quality metric to a signal quality metric threshold; and determine the linear correlation between the blood pressure signal and the oxygen saturation signal only while the signal quality metric is above a signal quality metric threshold.

16. A system for monitoring autoregulation, the system comprising:
- an oxygen saturation sensor configured to obtain an oxygen saturation signal indicative of blood oxygen saturation of a patient;
- a controller comprising one or more processors configured to:
  - receive the oxygen saturation signal and a blood pressure signal indicative of a blood pressure of the patient;
  - determine a linear correlation between the blood pressure signal and the oxygen saturation signal;
  - determine a significance value associated with the linear correlation, wherein the significance value comprises a p-value; and
  - provide a signal indicative of the patient's autoregulation status to an output device based on the linear correlation and the significance value.

17. The system of claim 16, wherein the oxygen saturation sensor is configured to generate the oxygen saturation signal and the blood pressure signal.

18. The system of claim 16, comprising the output device, wherein the one or more processors are configured to cause the output device to display a cerebral index value indicative of the patient's autoregulation status, an indication of a cerebral index value reliability, an indication of the patient's autoregulation status, or any combination thereof.

19. The system of claim 18, wherein the one or more processors are configured to provide an alarm signal to the output device, and the output device is configured to provide a visual or audible alarm based on the alarm signal.

20. The system of claim 16, wherein the one or more processors are configured to:
- determine the significance value is above a predetermined threshold; and
- block transmission of the signal indicative of the patient's autoregulation status to the output device in response to determining the significance value is above the predetermined threshold.

* * * * *